United States Patent
Cadiz Bedini et al.

(10) Patent No.: US 10,940,456 B2
(45) Date of Patent: Mar. 9, 2021

(54) METHOD FOR PRODUCING HYDROGENATED AMORPHOUS SILICON-CONTAINING COLLOIDS AND/OR COMPOSITE COLLOIDS AND FOR ENCAPSULATING SUBSTANCES WITH HYDROGENATED AMORPHOUS SILICON-CONTAINING COMPOSITE COLLOIDS, HYDROGENATED AMORPHOUS SILICON-CONTAINING COLLOIDS AND/OR COMPOSITE COLLOIDS, SUBSTANCES ENCAPSULATED WITH SILICON-CONTAINING COMPOSITE LAYERS, AND USE THEREOF

(71) Applicant: Forschungszentrum Juelich GmbH, Juelich (DE)

(72) Inventors: Andrew Paolo Cadiz Bedini, Reutlingen (DE); Benjamin Klingebiel, Linnich (DE); Stefan Haas, Baesweiler (DE); Jan Flohre, Aachen (DE); Reinhard Carius, Juelich (DE); Chunguang Chen, Juelich (DE); Peter Notten, Waalre (NL)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/753,800

(22) PCT Filed: Oct. 30, 2018

(86) PCT No.: PCT/DE2018/000320
§ 371 (c)(1),
(2) Date: Apr. 6, 2020

(87) PCT Pub. No.: WO2019/091506
PCT Pub. Date: May 16, 2019

(65) Prior Publication Data
US 2020/0254416 A1    Aug. 13, 2020

(30) Foreign Application Priority Data
Nov. 7, 2017  (DE) .................. 10 2017 010 263.5

(51) Int. Cl.
*B01J 13/04*  (2006.01)
*C01B 32/956*  (2017.01)
(Continued)

(52) U.S. Cl.
CPC ........... *B01J 13/04* (2013.01); *B01J 13/0086* (2013.01); *C01B 32/956* (2017.08);
(Continued)

(58) Field of Classification Search
None
See application file for complete search history.

(56) References Cited

U.S. PATENT DOCUMENTS

2013/0297997 A1    11/2013  Stanley
2016/0015652 A1*    1/2016  John ..................... C09B 11/24
                                                                424/490
2016/0297997 A1*   10/2016  Cadiz Bedini ....... C09D 183/16

FOREIGN PATENT DOCUMENTS

EP          1867993 A1    12/2007
EP          3026736 B1     6/2016
WO     WO 2015085980 A1    6/2015

OTHER PUBLICATIONS

Bedini, et al. "Liquid Hydridosilane Prescursor Prepared from Cyclopentasilane via Sonication at Low Temperatures Without the Action of Light," *Ultrasonics Sonochemistry* 34, 26: 289-293 (May 26, 2016).
(Continued)

*Primary Examiner* — Jeffrey D Washville
(74) *Attorney, Agent, or Firm* — Leydig, Voit & Mayer, Ltd.

(57) ABSTRACT

Hydrogenated amorphous silicon-containing colloids or composite colloids have a silicon-containing shell which
(Continued)

surrounds the hollow colloids or composite colloids. The colloids have a spherical geometry. The silicon-containing composite colloids have a spherical geometry and a diameter of between 2 nm and 7 nm in scanning electron micrographs, and the silicon-containing colloids have a spherical geometry with a cavity and a diameter of between 50 and 200 nm in scanning transmission electron micrographs. The cavity is surrounded by a shell with a thickness of between 3 and 10 nm.

20 Claims, 15 Drawing Sheets

(51) Int. Cl.
*C01B 33/027* (2006.01)
*B01J 13/00* (2006.01)
*B82Y 5/00* (2011.01)
*B82Y 30/00* (2011.01)
*B82Y 40/00* (2011.01)

(52) U.S. Cl.
CPC ............... *C01B 33/027* (2013.01); *B82Y 5/00* (2013.01); *B82Y 30/00* (2013.01); *B82Y 40/00* (2013.01); *C01P 2002/02* (2013.01); *C01P 2002/85* (2013.01); *C01P 2004/03* (2013.01); *C01P 2004/04* (2013.01); *C01P 2004/34* (2013.01); *C01P 2004/61* (2013.01); *C01P 2004/62* (2013.01); *C01P 2004/64* (2013.01); *C01P 2006/40* (2013.01)

(56) References Cited

OTHER PUBLICATIONS

Guruvenket, et al. "Synthesis of Silicon Quantum Dots Using Cyclohexasilane (Si6H12)," *Journal of Materials Chemistry C* 4: 8206-8213 (Jul. 28, 2016).

Pell, et al. "Synthesis of Amorphous Silicon Colloids by Trisilane Thermolysis in High Temperature Supercritical Solvents," *Langmuir* 20, 16: 6546-6548 (Jul. 8, 2004).

* cited by examiner

METHOD FOR PRODUCING HYDROGENATED AMORPHOUS SILICON-CONTAINING COLLOIDS AND/OR COMPOSITE COLLOIDS AND FOR ENCAPSULATING SUBSTANCES WITH HYDROGENATED AMORPHOUS SILICON-CONTAINING COMPOSITE COLLOIDS, HYDROGENATED AMORPHOUS SILICON-CONTAINING COLLOIDS AND/OR COMPOSITE COLLOIDS, SUBSTANCES ENCAPSULATED WITH SILICON-CONTAINING COMPOSITE LAYERS, AND USE THEREOF

CROSS-REFERENCE TO PRIOR APPLICATIONS

This application is a U.S. National Phase application under 35 U.S.C. § 371 of International Application No. PCT/DE2018/000320, filed on Oct. 30, 2018, and claims benefit to German Patent Application No. 10 2017 010 263.5, filed on Nov. 7, 2017. The International Application was published in German on May 16, 2019 as WO 2019/091506 A1 under PCT Article 21(2).

FIELD

The invention relates to a method for producing hydrogenated amorphous silicon-containing colloids and/or composite colloids and for encapsulating substances with hydrogenated amorphous silicon-containing composite layers, as well as to hydrogenated amorphous silicon-containing colloids and/or composite colloids and to substances encapsulated with silicon-containing composite layers and to the use thereof. The invention further relates to hydrogenated amorphous silicon-containing colloids and/or composite colloids which are hollow and have a silicon-containing shell.

BACKGROUND

According to the prior art, gaseous, lower silanes, i.e., silicon hydrogen compounds, such as monosilane ($SiH_4$) and disilane ($Si_2H_6$), are used as precursors to produce silicon-containing nanoparticles by means of vacuum processes, such as PECVD (plasma-enhanced chemical vapor deposition), hot wire CVD or hot wall reactors.

A method as described in L. E. Pell, et al., "Synthesis of amorphous silicone colloids by trisilane thermolysis in high temperature supercritical solvents," Langmuir 20 (2004) 6546-6548, discloses a method in which amorphous and hydrogen-containing colloids are produced in an autoclave at temperatures of between 400° C. and 500° C. and pressures of between 200 bar and 400 bar.

For cyclohexasilane ($Si_6H_2$), a gas-phase pyrolysis method is known which allows for producing amorphous and hydrogen-containing nanoparticles but which is carried out at temperatures of between 900° C. and 1100° C. The method is described in the publication "Synthesis of silicon quantum dots using cyclohexasilane ($Si_6H_2$)," Guruvenket et al., J. Mater. Chem. C, 2016, 4, 8206.

Such methods do not allow for producing colloids or composite colloids at room temperature and atmospheric pressure based on liquid silicon-containing compounds and acoustic cavitation. Furthermore, such methods do not provide hydrogenated silicon-containing composite colloids which are hollow and hydrogenated without further chemical treatment steps and have a silicon-containing shell.

Various disadvantages are associated with the methods according to the prior art. The prior art methods usually lead to crystalline or non-hydrogenated nanoparticles. The methods are technically demanding and are based on gas-phase high-temperature or plasma or laser technology methods or require high pressure. These disadvantages of the prior art have the consequence, for example, that direct encapsulation of substances or foreign substances with hydrogenated amorphous silicon-containing coatings is not possible.

SUMMARY

Hydrogenated amorphous silicon-containing colloids or composite colloids, comprising a silicon-containing shell which surrounds hollow colloids or composite colloids, the colloids having a spherical geometry, the silicon-containing composite colloids having a spherical geometry and a diameter of between 2 nm and 7 nm in scanning electron micrographs, and the silicon-containing colloids having a spherical geometry with a cavity and a diameter of between 50 and 200 nm in scanning transmission electron micrographs, wherein the cavity is surrounded by a shell with a thickness of between 3 and 10 nm.

DETAILED DESCRIPTION

Figure 1:
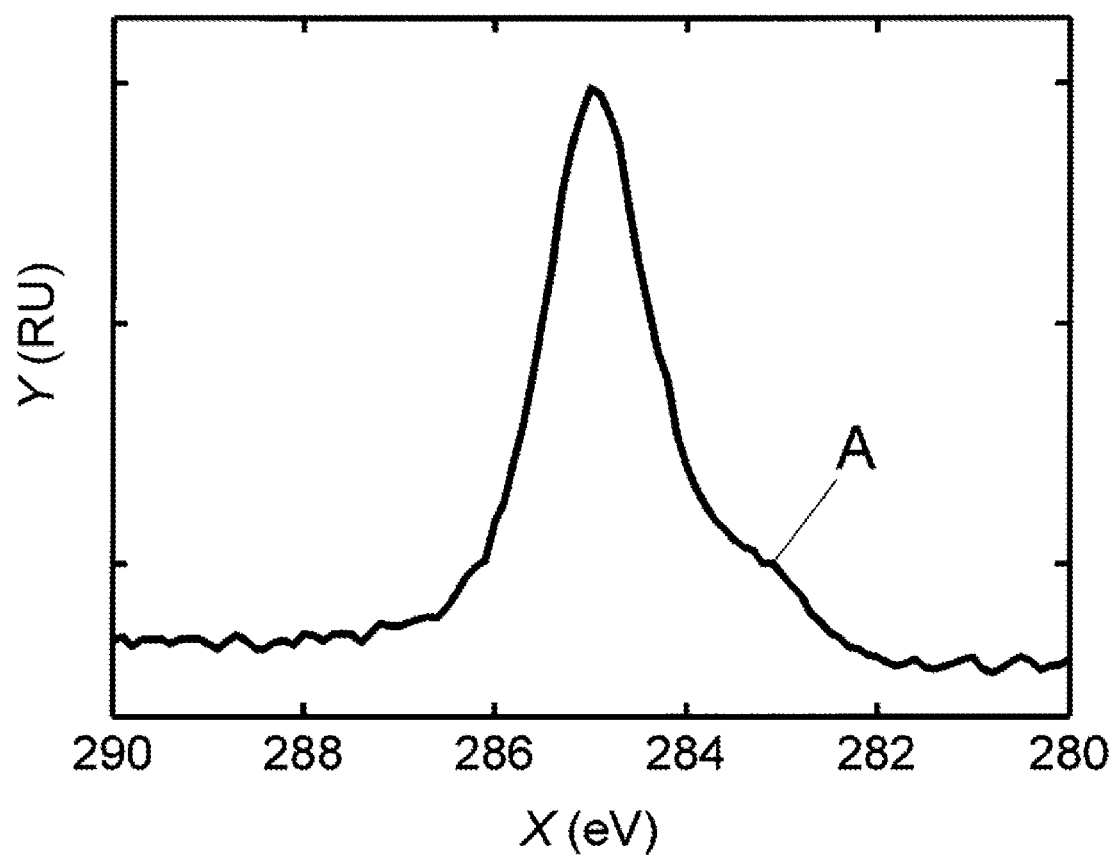
FIG. 1—X-ray photoelectron spectrum on silicon carbide composite colloids produced by sonication of a trisilane solution with 2-pentyne as additive.

An embodiment of the invention provides a method for producing hydrogenated amorphous silicon-containing composite colloids and for encapsulating substances with said hydrogenated amorphous silicon-containing composite colloids and to provide hydrogenated amorphous silicon-containing composite colloids and substances encapsulated with hydrogenated amorphous silicon-containing composite colloids and the use thereof. In particular embodiments of the invention, the method is carried out at low temperatures, such as room temperature, and lower pressures, such as atmospheric pressure. In certain embodiments of the invention, the method is simple to carry out and requires little equipment. In certain embodiments of the invention, the method enables the encapsulation or embedding of additives or substances with hydrogenated amorphous silicon-containing composite colloids or to allow them to be coated with hydrogenated amorphous silicon-containing composite colloids. Furthermore, hydrogenated amorphous silicon-containing composite colloids and substances encapsulated with hydrogenated amorphous silicon-containing coatings are to be provided in certain embodiments of the invention. Further embodiments of the invention provide hydrogenated amorphous silicon-containing or hydrogenated silicon-containing colloids and/or composite colloids which are hollow and have a silicon-containing shell.

The term "colloid" within the meaning of the present application is understood to mean both liquid and solid nanoparticles as well as liquid or solid particles with no nanoscale dimensions, such as microparticles or agglomerates. The colloids can be emulsions or suspensions of droplets or gases in a liquid which are converted to solid colloids during or after sonication/cavitation according to certain embodiments of the invention.

The term "composite colloid" within the meaning of the present application is understood to mean colloids consisting of more than just silicon, such as colloids in which, for example, a carbon or a medicament has been co-synthesized and/or embedded and/or encapsulated.

The term "encapsulation" within the meaning of the present application is generally understood to mean a coating or embedding of a substance with or in a colloid.

With the method according to certain embodiments of the invention, it is now possible to provide a method for producing hydrogenated amorphous silicon-containing colloids and/or composite colloids and for encapsulating substances with hydrogenated amorphous silicon-containing colloids and/or composite colloids as well as hydrogenated amorphous silicon-containing colloids and/or composite colloids and substances encapsulated with silicon-containing colloids and/or composite colloids and their use, which avoids the above-mentioned disadvantages. In particular, the method may be carried out at low temperatures, such as room temperature, and at lower pressures, such as atmospheric pressure. In certain embodiments of the invention, the method is simple to carry out and requires little equipment. In certain embodiments of the invention, the method also enables the encapsulation of substances with hydrogenated amorphous silicon-containing colloids and/or composite colloids or with hydrogenated amorphous silicon-containing coatings. Furthermore, hydrogenated amorphous silicon-containing composite colloids and substances encapsulated with hydrogenated amorphous silicon-containing coatings can be provided. In certain embodiments of the invention, the method allows for producing hydrogenated amorphous silicon-containing colloids and composite colloids that are hollow and have a silicon-containing shell.

The colloids and composite colloids produced according to the method according to certain embodiments of the invention have additional advantageous properties.

Preferably, the silicon-containing colloids and/or composite colloids according to certain embodiments of the invention have a spherical geometry. A silicon-containing or a hydrogenated silicon-containing shell surrounds the cavity of the colloids and/or composite colloids. The colloids and/or composite colloids preferably have a diameter of between 50 and 200 nm. The silicon-containing shell preferably has a thickness in the range from 3 to 10 nm.

For example, not only the volume but also the outer surface can be terminated with different hydrogen-containing groups, namely with —SiH, —$SiH_2$ and —$SiH_3$ groups. Moreover, since the surface is in a non-oxidized state (with oxygen), the particular properties of the surfaces considerably facilitate the effort of functionalizing the surface chemistry of the colloids and/or composite colloids.

A further advantageous property of the colloids and/or composite colloids is the nanoporous or mesoporous arrangement according to certain embodiments of the invention, which they have as thin layers on solid substrates. According to the application, such layers can be produced by means of spin coating, drop coating, spray coating, doctor blade coating or knife coating. Without any addition of binding or conductivity agents, said porous layers produced according to certain embodiments of the invention have surprisingly high specific capacities and long stabilities in case of lithiation in lithium ion half-cells.

In the following, embodiments of the invention are described, without this being interpreted restrictively.

According to the method according to certain embodiments of the invention, a hydridosilane or a hydrodosilane derivative or a mixture of various hydridosilanes and/or hydridosilane derivatives dissolved either in at least one organic and/or inorganic solvent or at least one hydridosilane or one hydrodosilane derivative or a mixture of various hydridosilanes and/or hydridosilane derivatives already present in liquid form without solvent is subjected to cavitation. Cavitation can be produced, for example, by a magnetostrictive or piezoelectric ultrasonic source and/or by a liquid-operated or gas-operated acoustic transducer.

According to certain embodiments of the invention, hydrogenated amorphous silicon-containing composite colloids are formed in the process. Colloids within the meaning of the present application are also to be understood to mean, for example, solids or particles or aggregates or agglomerates which have a size of between 0.1 nm and 100 μm in at least one length dimension.

According to certain embodiments of the invention, the following compounds can be used as hydridosilanes: linear or branched silanes of the empirical formula $Si_nH_{2n+2}$, with n=1, 2, 3, . . . , or cyclic silanes of the form $Si_nH_{2n}$, with n=5, 6, . . . .

For example, at least one component from the group consisting of linear or branched silanes with the empirical formula $Si_nH_{2n+2}$ (with n≥2) or cyclic silanes with the empirical formula $Si_nH_{2n}$ (with n>4) or from organosilanes, halosilanes or organohalosilanes, preferably from the group of trisilane, tetrasilane, pentasilane, hexasilane, heptasilane, cyclopentasilane, cyclohexasilane, neopentasilane, trichlorosilane, or also liquid germanes ($Ge_nH_{2n+2}$, with n≥2) can be used as hydridosilanes.

According to certain embodiments of the invention, the following compounds can be used as hydridosilane derivatives: compounds of the general formula $SiH_nX_{4-n}$ (with X=F, Cl, Br, I, $CH_3$ and 1<n<4).

Mixed solution is to be understood as meaning solutions comprising mixtures of various hydridosilanes or of various hydridosilane derivatives or a combination of hydridosilanes and hydridosilane derivatives.

It is also possible to use at least two hydridosilanes so that the composite colloid produced by the method is a subcombination of at least two components, in particular of the aforementioned hydridosilanes.

With the method of certain embodiments of the invention, microbubbles produced by cavitation implode in the solution.

Both organic and inorganic solvents are suitable as solvents. Examples of suitable solvents to be used include linear (n) and iso (i) alkanes, such as n-pentane or i-pentane ($C_5H_{12}$), n-hexane or i-hexane ($C_6H_{14}$), as well as cyclic alkanes, such as cyclohexane ($C_6H_{12}$), cycloheptane ($C_7H_{14}$), cyclooctane ($C_8H_{16}$), or aromatic compounds, such as benzene, toluene, xylene, naphthalene.

Oxygen-containing or inorganic compounds, such as water, alcohols, ethers, alkoxyalkanes, siloxanes can also be used as solvents.

However, all other organic solvents that are suitable according to the prior art and known to the person skilled in the art, in particular high-boiling solvents, such as higher alkanes, or terpenes, such as n-dodecane or squalene, can also be used. A solvent mixture of at least two components, in particular the solvents mentioned above, can also be used as the solvent.

The method can be carried out in a temperature range between −120° C. and 250° C. A temperature range between −30° C. and 125° C. is preferred. The method can be carried out, in particular, at ambient temperature, in particular at room temperature.

The method can be carried out in a pressure range between 0.5 bar and 1000 bar. A pressure range between 1 bar and 100 bar is preferred. The method can be carried out, in particular, at normal pressure, especially at atmospheric pressure.

The ultrasound may, for example, be in a frequency range of 15 kHz to 50 MHz but is not limited to this range.

In a further embodiment of the invention, the solution may also contain additives. The term "additives" within the meaning of the present invention is to be understood as meaning substances which when used in a solution before, during, or after sonication, lead to no and/or weak and/or strong chemical bonds with the hydrogen and/or the silicon of the colloids produced.

Additives which lead to chemical bonds can be solid, liquid or gaseous substances, such as lithium-containing compounds or dopants, such as boron-containing and/or phosphorus-containing compounds, or compounds of all types which convert to corresponding compositions, alloys or composite colloids. The term "composite colloid" is to be understood to mean colloids which by the method according to certain embodiments of the invention consist not only of hydrogen and silicon.

Additives which are to establish no and/or only weak chemical bonds with the hydrogen and/or with the silicon of the colloids produced can be solid, liquid or gaseous molecules, such as nanoparticles or therapeutics.

These additives are also referred to as substances "to be encapsulated" or "to be coated." If these substances are located within and/or on the surface of the colloid produced, this process is understood within the context of the present application as an "embedding" or "encapsulation" or as "coating." In contrast to encapsulation, it is possible in the case of coating that the coating constitutes an imperfect encapsulation in which the substances are not 100% inside and/or on the surface of the colloid produced. An aim of the invention is to preserve the original target effect of these substances in part or in full. Preferably, the substances to be embedded or encapsulated should be so small as to fit into the bubbles produced by cavitation. They should therefore advantageously have a diameter of <100 μm.

In the case of coating, the substances can also have a larger diameter of >100 μm since these substances are gradually coated on the surface of the composite colloids by being added during sonication or during implosion of the cavitation bubbles in the vicinity of these bubbles. The additives or substances result in that silicon-containing compositions and composite colloids can be synthesized. At least one additive can be added to the solution, but it is also possible to use a combination of at least two additives, in particular of the additives mentioned. In order to produce the composite colloids, the additives can be added before or during synthesis of the hydridosilane solution.

The concentration of the hydridosilane or hydridosilanes in the solvent may be between 0 and 100 wt. %. When using a hydridosilane solution without additives, a hydridosilane concentration of, for example, 0.1-50 wt. % is used; the remainder is solvent. When using a hydridosilane solution with additives, an additives concentration of, for example, 0.01-50 wt. % is used. The remainder consists of hydridosilanes and solvents.

With this method, it is possible to produce composite colloids of a particle size in a range of 0.5 nm to 10 μm, especially in a range of 1.5 nm to 1 μm.

The method allows for the production according to certain embodiments of the invention of special colloids with advantageous properties, such as the formation of agglomerates and aggregates larger than 200 nm, by means of long sonication times and/or filtering or separation methods, for example by applying membrane filters or centrifugation and/or subsequent thermal and/or photolytic treatment. In a further embodiment, additives or substances coated with hydrogenated amorphous silicon-containing coatings can be produced with the method according to certain embodiments of the invention.

To this end, in certain embodiments, at least one substance is added to the solution comprising the solvent and the hydridosilane and optionally at least one additive, which substance is to be coated with hydrogenated amorphous silicon-containing material by the action of the ultrasound on the solution.

The additives or substances to be encapsulated may be solid and/or liquid and/or gaseous.

The additives or the substances to be coated and/or embedded and/or encapsulated may be nanoparticles and/or colloids comprising, without limitation, Au, c-Si, CdSe, CuO, $Cu_2O$, $Cu_2S$, CuS, $Fe_3O_4$, $Fe_2O_3$, FeS, $FeS_2$, $FeSi_2$, Li, LiH, SnS, ZnS, ZrS and also molecules, such as alendronates, cisplatinum, doxorubicin, epirubicin, fluorouracil, idarubicin, as well as compounds from the group of pentynes, such as 1-pentyne or 2-pentyne, or boranes, such as diborane, pentaborane or decaborane, white phosphorus or also general compounds, such as phosphanes or phosphines. It is also possible to use at least two substances, in particular from the group of the additives or substances mentioned, in order to produce mixtures of substances coated therewith.

With the method according to certain embodiments of the invention, additives or substances in solution can be embedded or encapsulated directly implosively in a casing of hydrogenated amorphous silicon-containing colloids. This is not possible with other methods since standard particle syntheses are based on traditional photolytic and/or thermolytic processes or growth by means of nucleation mechanisms.

Composite colloids within the meaning of the application are also understood to be colloids that are synthesized by means of cavitation using solid and/or liquid and/or gaseous additives or substances, and where the additives or substances are fully encapsulated with hydrogenated amorphous silicon-containing coatings or partly or fully coated with hydrogenated amorphous silicon-containing layers. The additives or substances can be present in the composite colloid with or without chemical bonds to the hydrogen and/or silicon.

Since the method of certain embodiments of the invention is a liquid-phase process that can be carried out at room or low temperatures and normal pressure, high-vacuum technology is not required.

In an embodiment of the method, the production of the hydrogenated amorphous silicon-containing colloids should preferably be carried out in an Ar or $N_2$ atmosphere, such as in a glove box with $H_2O$ and $O_2$ concentrations of typically <10 ppm.

Certain embodiments of the invention allow for the direct embedding and/or encapsulation of substances that may be present within imploding microbubbles.

The hydrogenated amorphous silicon-containing composite colloids obtained according to certain embodiments of the invention can be used, for example, in photovoltaic or photocatalytic applications as light absorber and/or doping material or plasmonic reflection gratings or diffuser layers for sensors, quantum dot light-emitting diodes, waveguides, singlet oxygen production, sewage treatment, as anode material in energy-storing applications, such as lithium ion, sodium ion, or lithium sulfide battery cells. The substances obtained according to certain embodiments of the invention and coated or encapsulated with hydrogenated amorphous silicon-containing colloids and/or composite colloids can be used for in vitro or in vivo medicament carriers, for in vitro or in vivo photofluorescent or magnetic resonance imaging methods as fluorescent markers and/or magnetic resonance imaging markers or contrast agents, as in vitro or in vivo therapeutic, medicament carrier and/or hyperthermia therapeutic, or in photodynamic therapy.

In particular, the colloids and/or the composite colloids and/or the coated or encapsulated substances can be used for solar cells, anodes for lithium ion battery cells and as therapeutics in the biomedical or nanomedical field.

According to certain embodiments of the invention, composite colloids and substances encapsulated with hydrogenated amorphous silicon-containing composite colloids are provided, which are characterized in that they can be produced by the method according to certain other embodiments of the invention.

In one embodiment of the method, a sintering and/or crystallization in a hydrogen-containing and/or low-pressure atmosphere can be carried out after coating.

In a further embodiment of the method, UV irradiation and/or microwave irradiation and/or active cooling can be carried out during production.

In a particularly preferred embodiment, the colloids or composite colloids according to the invention are produced from trisilane using deionized water as solvent. The nanoparticles thus produced are hydrophilic and form stable dispersions in the water and are both oxidized and hydrogenated.

certain embodiments of the invention are explained in more detail below based on exemplary embodiments and figures, without the object of the invention being limited thereby.

Exemplary Embodiments

Example 1—X-Ray Photoelectron Spectrum on Silicon Carbide Composite Colloids Produced by Sonicating a Trisilane Solution with 2-Pentyne as Additive The synthesis of silicon carbide composite colloids according to certain embodiments of the invention is shown on the basis of X-ray photoelectron spectroscopy (XPS) measurement illustrated in FIG. 1. The XPS spectrum shows the C1s peak of carbon. The abscissa X indicates the binding energy in (eV) and the ordinate V indicates the XPS intensity in relative units (RU). The cyclooctane solution used has a trisilane concentration of 25 vol. % and the additive used was 2-pentyne with a concentration of 13 vol. %. The conditions for sonication according to certain embodiments of the invention were as follows: process temperature=8° C., sonication duration=320 min, sonotrode amplitude=216 µm. The dried composite colloids were measured on a gold-coated glass substrate. Component (A) at about 283 eV in FIG. 1 points to silicon carbon bonds. Consequently, embedding of carbon atoms in silicon-containing composite colloids can be found.

Example 2—Scanning Electron Micrograph of Silicon Carbide Composite Colloids

Figure 2:
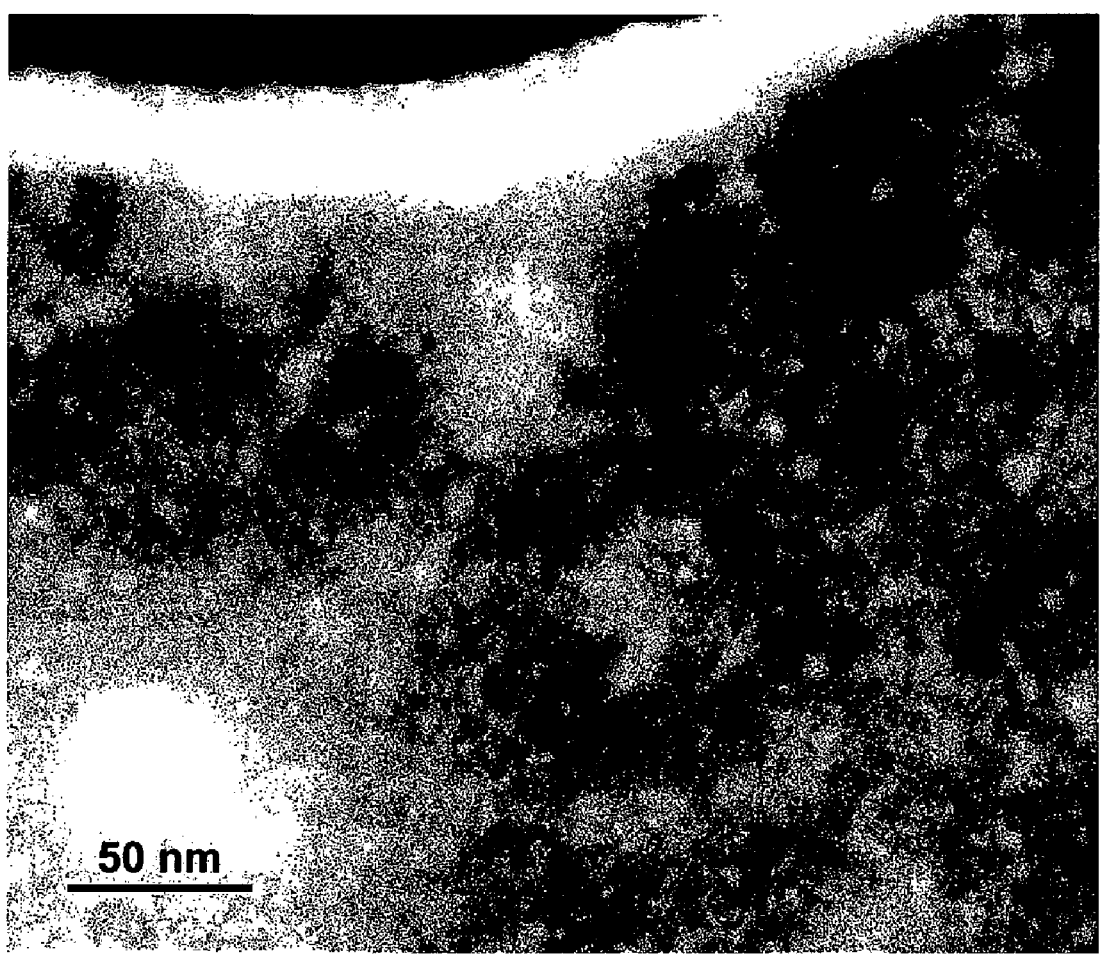
FIG. 2—Transmission electron micrograph of silicon carbide composite colloids.

In order to illustrate the silicon carbide composite colloids from Example 1, a scanning electron micrograph is shown in FIG. 2. The nanoparticles are spherical and have diameters of between 2 nm and 7 nm.

Figure 3:
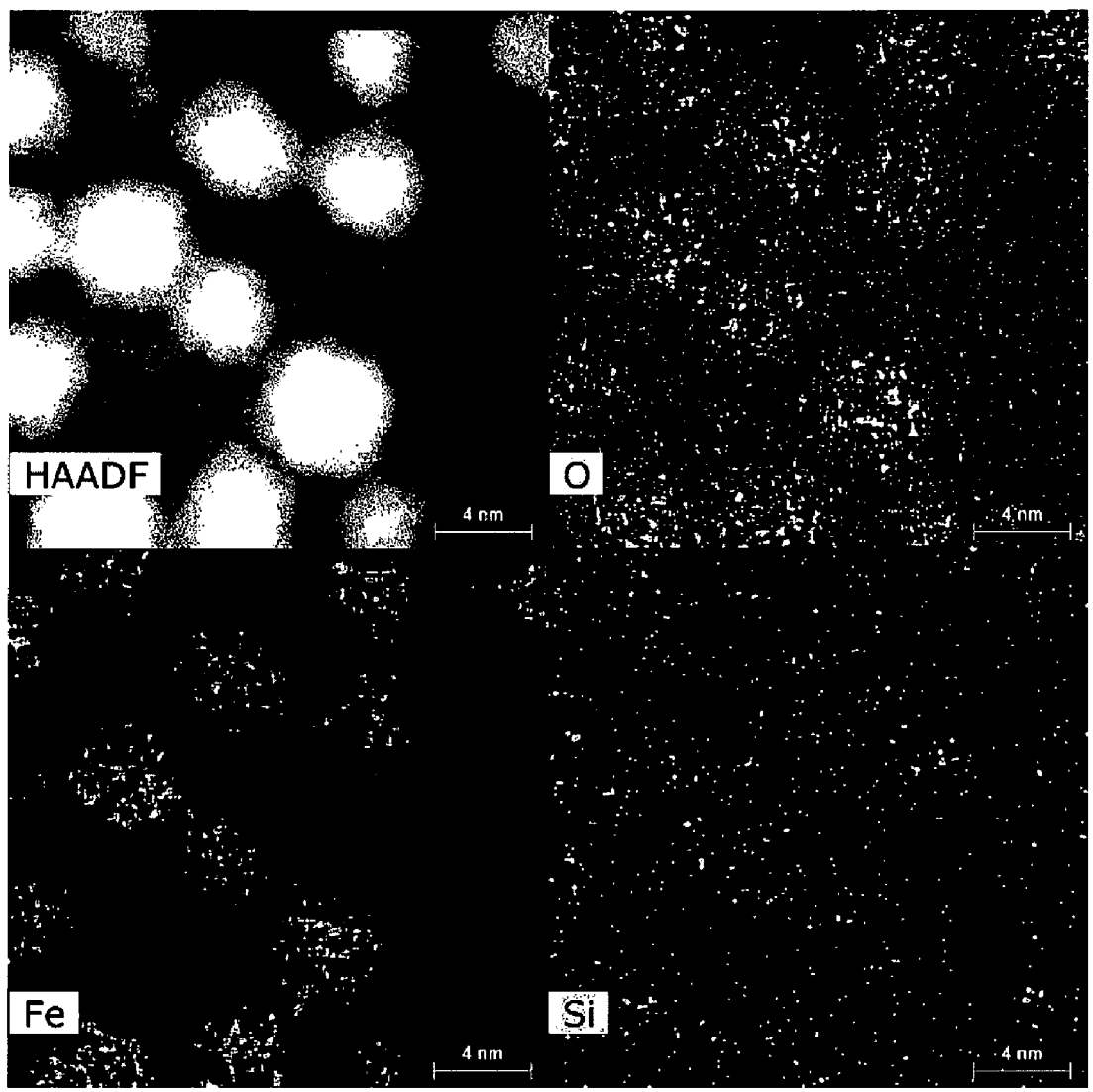
FIG. 3—Scanning transmission electron micrograph and elemental analysis by means of energy-dispersive X-ray spectroscopy of $Fe_3O_4$ nanoparticles without sonication according to certain embodiments of the invention.

Example 3—Scanning Transmission Electron Micrograph and Elemental Analysis by Means of Energy-Dispersive X-Ray Spectroscopy of $Fe_3O_4$ Nanoparticles without Sonication According to Certain Embodiments of the Invention The scanning transmission electron micrograph in FIG. 3 (HAADF) on the upper left-hand side shows $Fe_3O_4$ nanoparticles on a carbon lattice that were extracted from an untreated trisilane cyclooctane solution. The remaining images taken by means of energy-dispersive X-ray spectroscopy show space-resolved element-specific distributions of oxygen (O), iron (Fe) and silicon (Si). There is no local correlation between the Si distribution and the position of the $Fe_3O_4$ nanoparticles. Consequently, no conclusion can be drawn as to a coating or encapsulation of the $Fe_3O_4$ nanoparticles with silicon.

Figure 4:
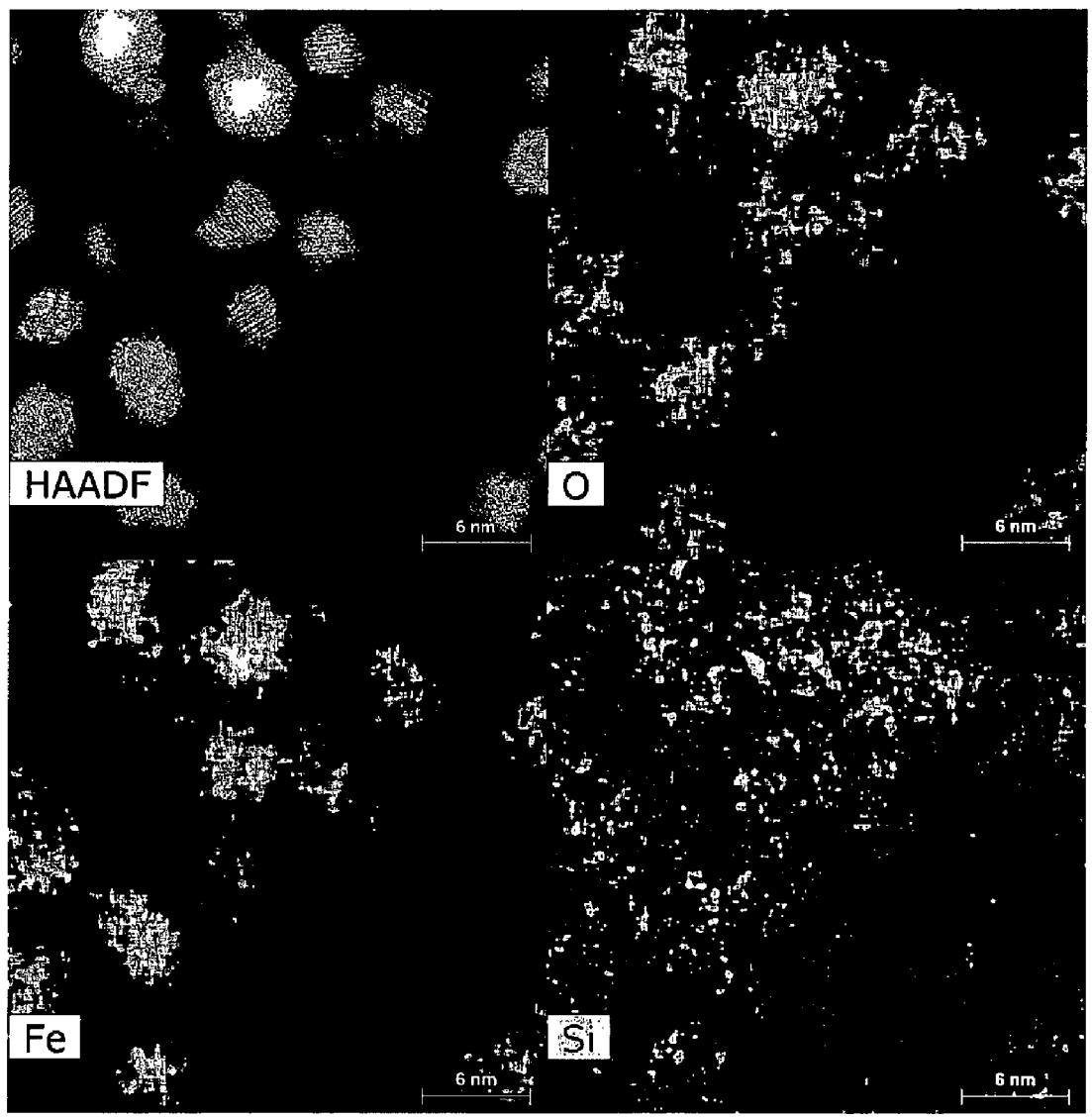
FIG. 4—Scanning transmission electron micrograph in FIG. 4 (HAADF) and elemental analysis by means of energy-dispersive X-ray spectroscopy of $Fe_3O_4$ nanoparticles coated with a thin silicon layer after sonication according to certain embodiments of the invention.

Example 4—Scanning Transmission Electron Micrograph in FIG. 4 (HAADF) and Elemental Analysis by Means of Energy-Dispersive X-Ray Spectroscopy of $Fe_3O_4$ Nanoparticles Coated with a Thin Silicon Layer after Sonication According to Certain Embodiments of the Invention The scanning transmission electron micrograph on the upper left-hand side shows $Fe_3O_4$ nanoparticles on a carbon lattice that were extracted from the solution of Example 3 after 140 minutes of sonication at a sonotrode amplitude of 230 μm. The remaining images taken by means of energy-dispersive X-ray spectroscopy show space-resolved element-specific distributions of oxygen (O), iron (Fe) and silicon (Si). A local correlation between the Si distribution and the position of the $Fe_3O_4$ nanoparticles can be seen. Consequently, a coating or encapsulation of the $Fe_3O_4$ nanoparticles with silicon can be found.

Figure 5:
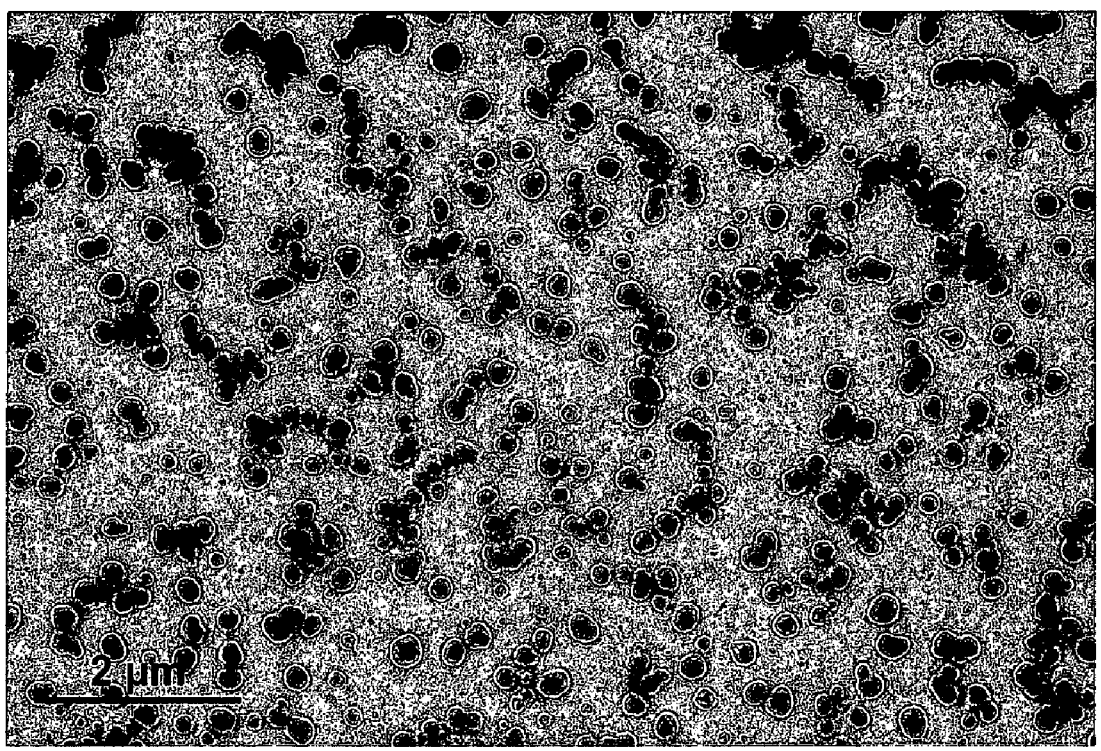
FIG. 5—Scanning electron micrograph of silicon-containing colloids produced according to certain embodiments of the invention.

Example 5—Scanning Electron Micrograph of Silicon-Containing Colloids Produced According to Certain Embodiments of the Invention at Low Temperature As shown in the scanning electron micrograph of FIG. 5, sonication at a temperature of approx. −3° C. and subsequent filtering (0.1 μm PTFE syringe filter) results in the production of, inter alia, well-defined, approx. 200 nm large silicon-containing colloid agglomerates.

Figure 6:
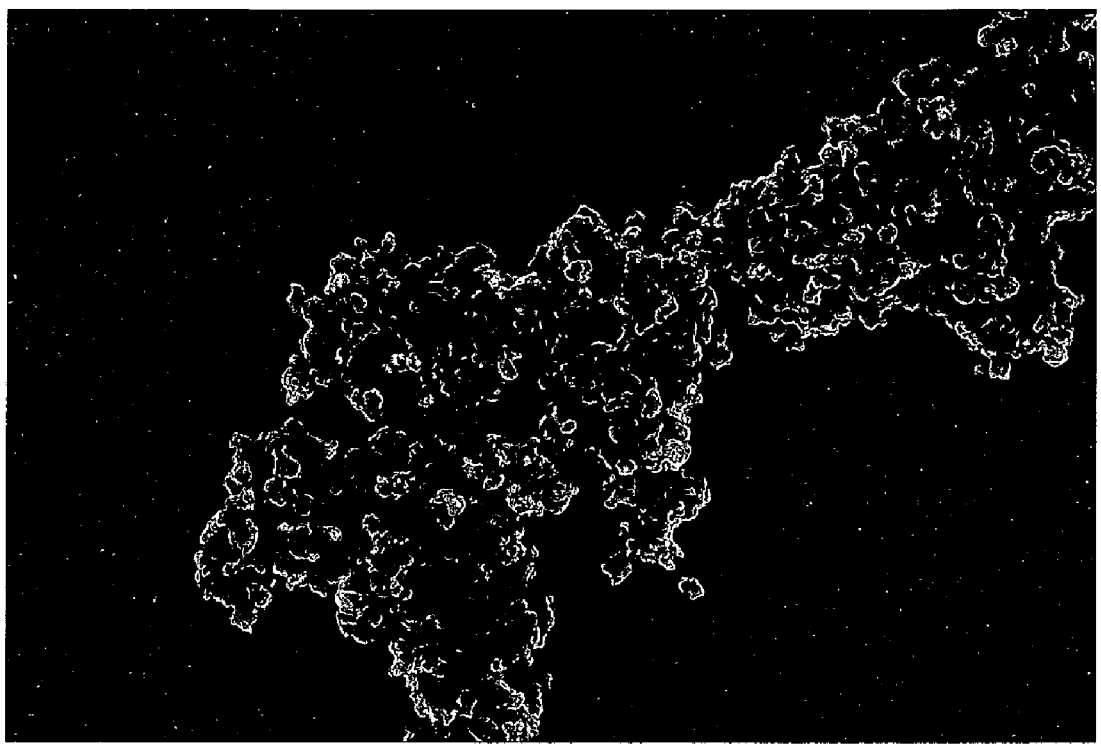
FIG. 6—Scanning electron micrograph of a silicon-containing coral-type colloid produced according to certain embodiments of the invention after tempering.

Example 6—Scanning Electron Micrograph of a Silicon-Containing Coral-Type Colloid Produced According to Certain Embodiments of the Invention after Tempering The scanning electron micrograph of FIG. 6 shows silicon-containing colloids after drop coating and subsequent tempering at approx. 450° C. for 20 minutes. The morphology assumes a coral-type shape.

Figure 7:
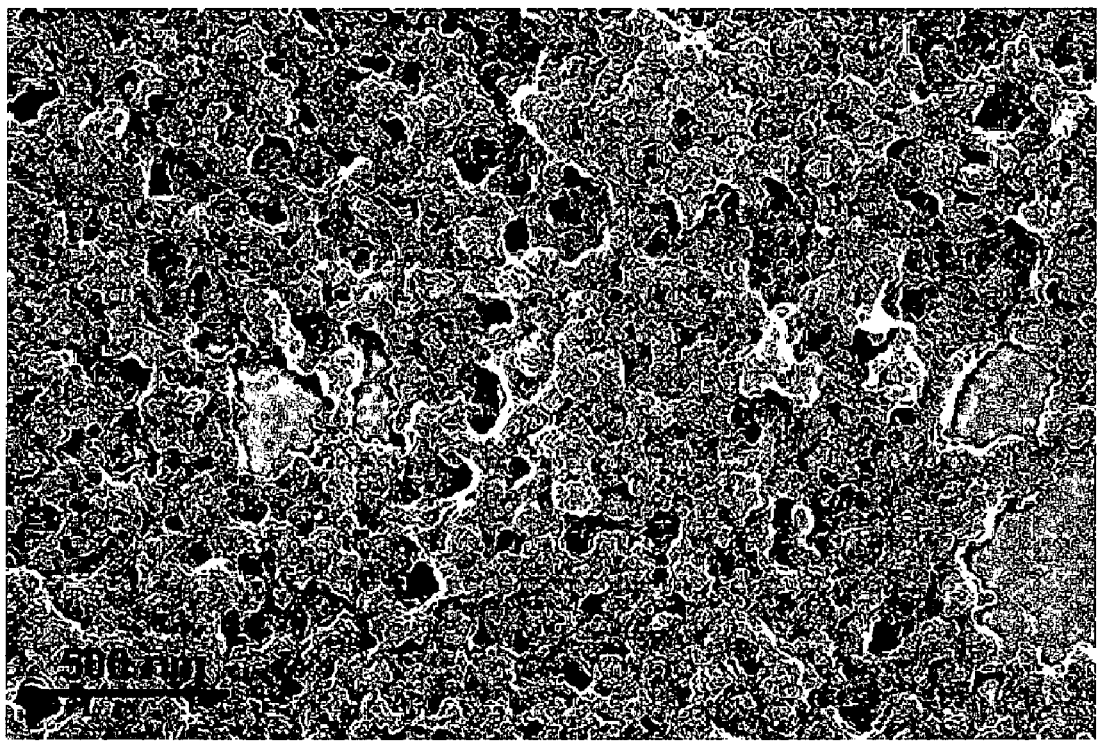
FIG. 7—Scanning electron micrograph of a highly porous layer of silicon-containing colloids produced at room temperature by spin coating.

Example 7—Scanning Electron Micrograph of a Highly Porous Layer of Silicon-Containing Colloids Produced at Room Temperature by Spin Coating The scanning electron micrograph of FIG. 7 shows silicon-containing colloids after spin coating at room temperature. The colloid layer has a sponge-like morphology.

Figure 8:
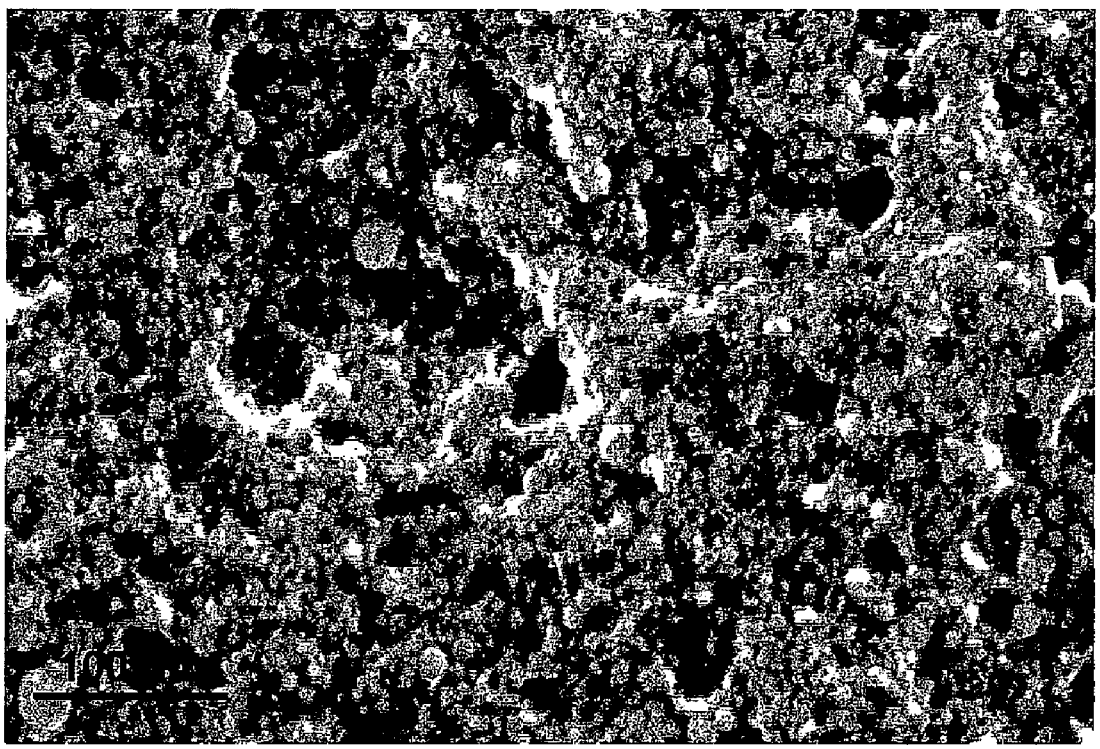
FIG. 8—Scanning electron micrograph close-up of a highly porous layer of silicon-containing colloids produced at room temperature by spin coating.

Example 8—Scanning Electron Micrograph Close-Up of a Highly Porous Layer of Silicon-Containing Colloids Produced at Room Temperature by Spin Coating The scanning electron micrograph close-up of FIG. 8 shows the highly porous morphology of thin silicon-containing colloid layers.

Figure 9:
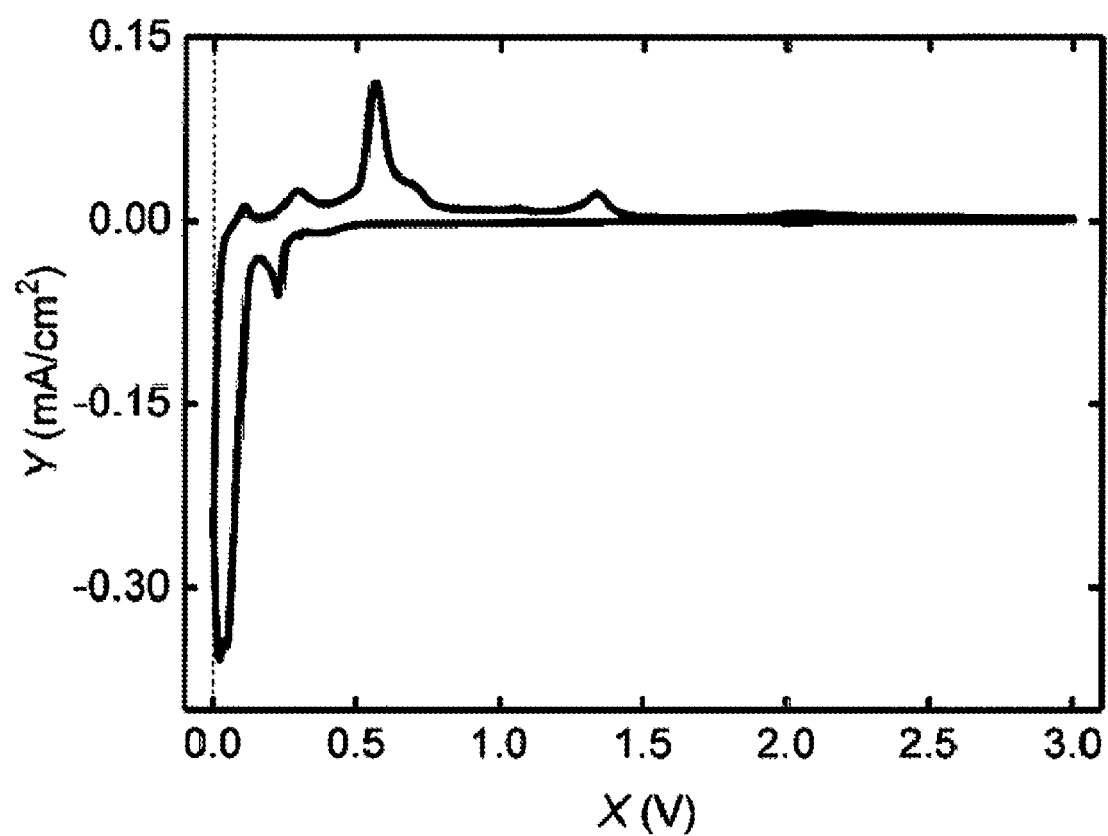
FIG. 9—Cyclic voltammetry measurement of the first lithiation or delithiation cycle of a porous thin-film anode made from silicon-containing composite colloids produced according to certain embodiments of the invention.
Figure 10:
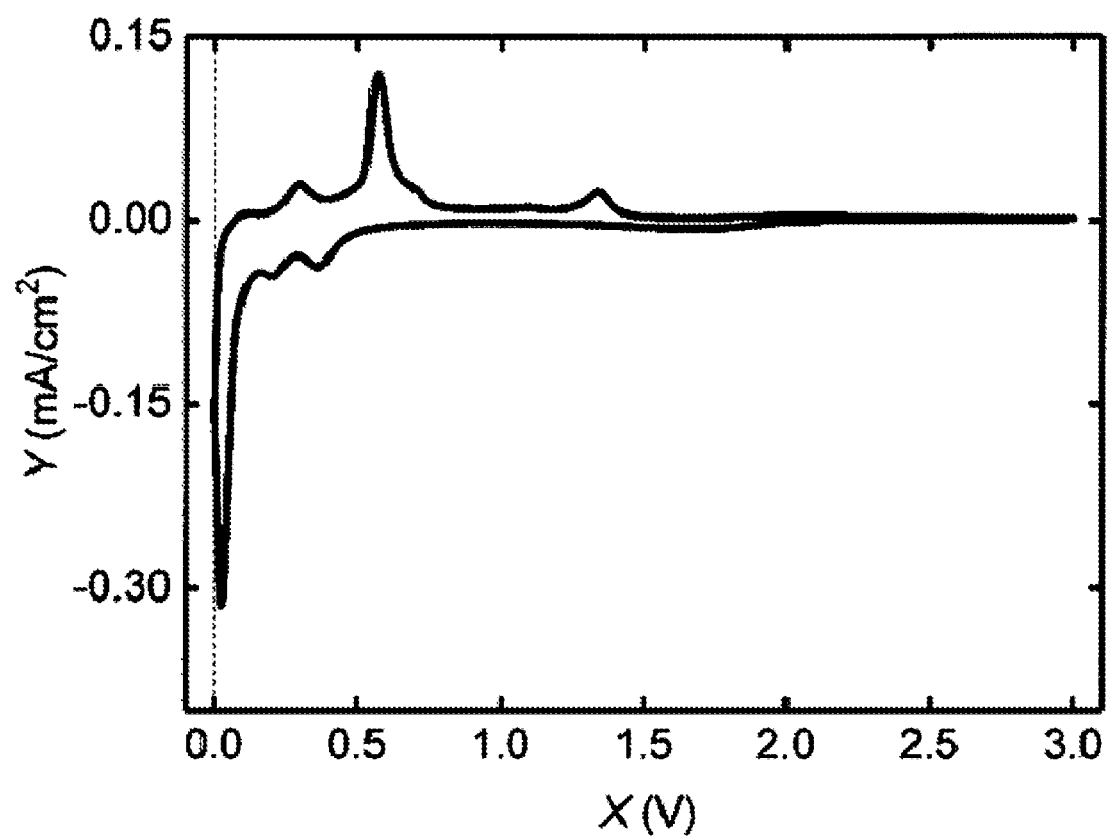
FIG. 10—Cyclic voltammetry measurement of the second lithiation or delithiation cycle of a porous thin-film anode made from silicon-containing composite colloids produced according to certain embodiments of the invention.

Example 9—Potentiostatic Cyclic Voltammetry Measurements on Porous Thin-Film Anodes Made from Silicon-Containing Composite Colloids Produced According to Certain Embodiments of the Invention FIG. 9 shows the first lithiation and/or delithiation cycle of an anode produced according to certain embodiments of the invention in a three-electrode arrangement with metallic lithium as reference electrode and counter electrode. The abscissa X indicates the voltage in (V) and the ordinate Y indicates the specific capacity in ($mA/cm^2$). The anode consists of silicon-containing composite colloids with between 10-15 at % carbon on the surface produced by tempering at 300° C. for 10 minutes. The electrolyte consists of 1 M $LiClO_4$ in propylene carbonate. The measurements were taken at 1 mV/s and the voltage is reported against $Li/Li^+$. FIG. 10 shows the second lithiation and/or delithiation cycle. No binders and/or conductive additives were used for the production of the anode.

Figure 11:
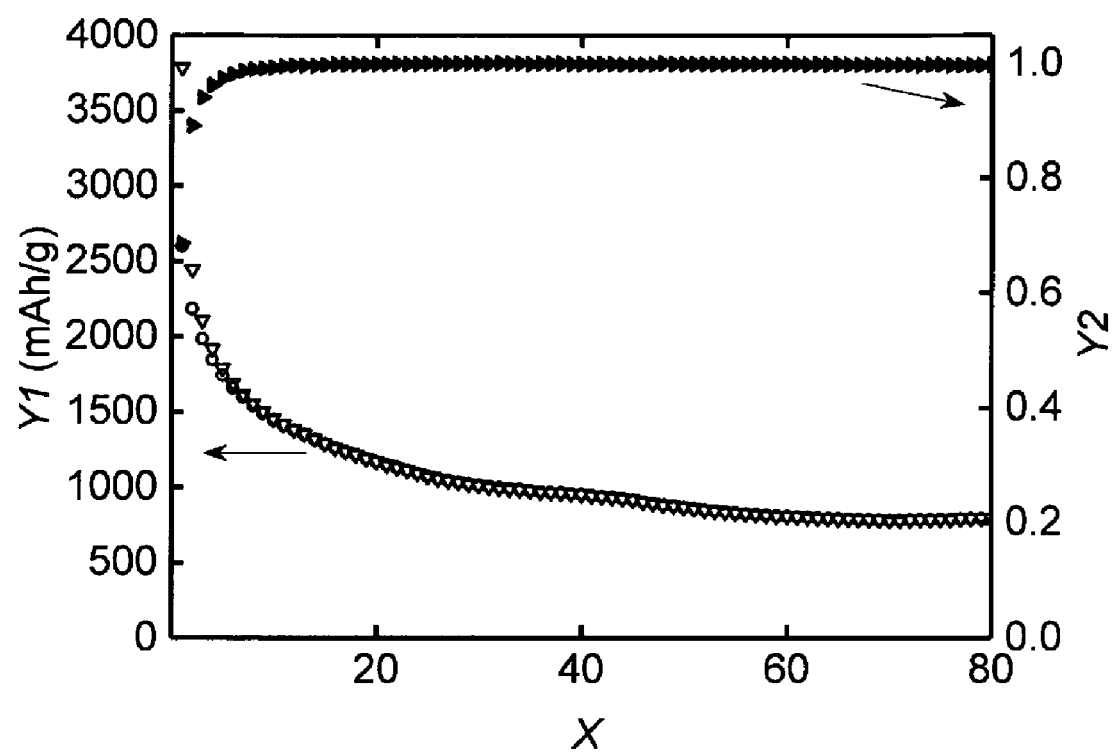
FIG. 11—Galvanostatic cyclization and Coulomb efficiency of a porous thin-film anode made from silicon-containing composite colloids produced according to certain embodiments of the invention.

Example 10—Galvanostatic Measurements on Porous Thin-Film Anodes Made of Silicon-Containing Nanoparticles Produced According to Certain Embodiments of the Invention FIG. 11 shows galvanostatic measurements at the anode of Example 9. The abscissa X indicates the cycle number and the ordinate Y1 indicates the specific capacity in ($mA/cm^2$). The ordinate Y2 indicates Coulomb efficiency. The measurements were carried out at a charging or discharging rate of 0.5 C (104.2 μA) with limiting voltages of 0 V and 3 V. Coulomb efficiency is more than 99.7% after 80 cycles.

Figure 12:
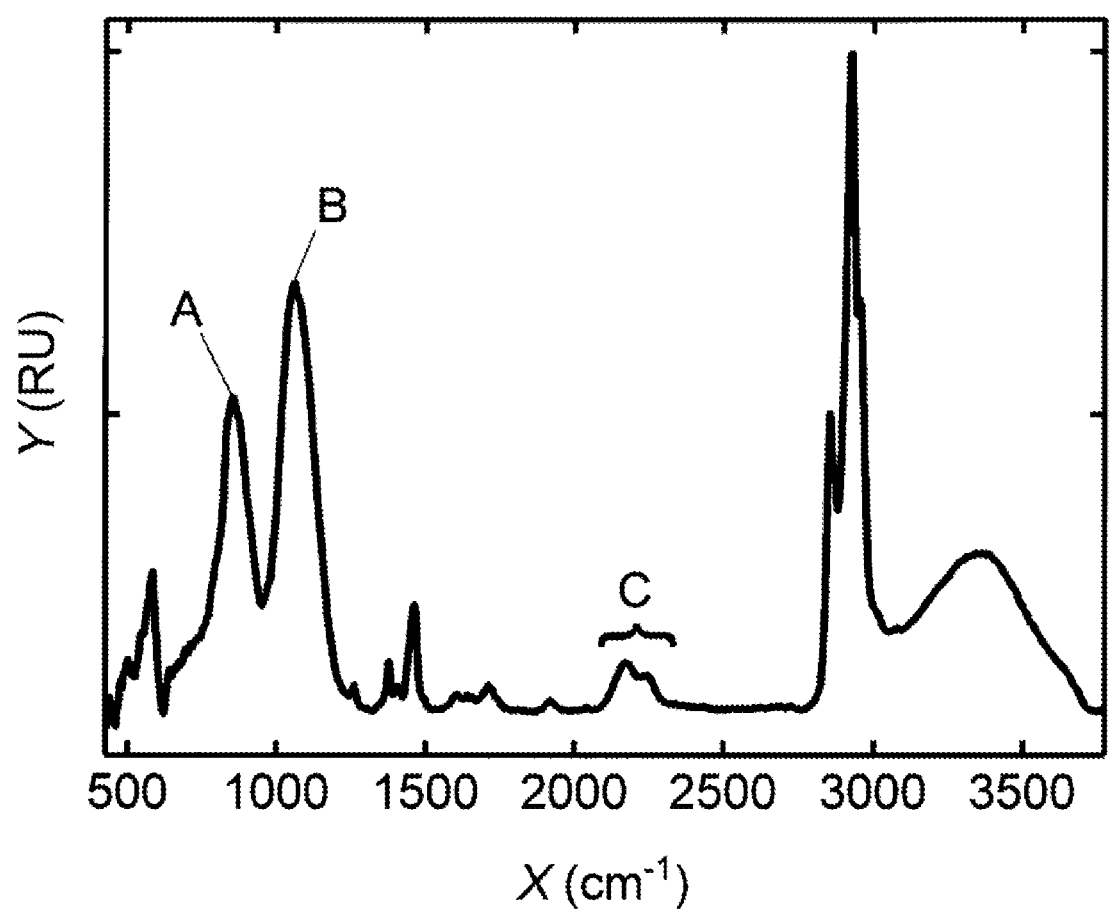
FIG. 12—Fourier-transform infrared spectrum of silane-containing composite colloids according to certain embodiments of the invention produced by sonication of a solution of trichlorosilane instead of trisilane.

Example 11—Fourier-Transformed Infrared Spectrum of Silane-Containing Composite Colloids According to Certain Embodiments of the Invention Produced by Sonication of a Solution of Trichlorosilane Instead of Trisilane FIG. 12 shows a Fourier-transformed infrared (FTIR) spectrum of silane-containing composite colloids produced from trichlorosilane. The composite colloids were applied to a silicon wafer, dried and then measured at room temperature. The abscissa X indicates the wavenumber in ($cm^{-1}$) and the ordinate Y indicates the FTIR signal intensity in relative units (RU). Mode (A) points to $Si-H_{1,2}$ flexural or scissor vibrations, mode (B) points to the Si—O—Si stretch vibrations and modes (C) point to $Si-H_{1,2}$ stretch vibrations. These modes are characteristic of amorphous silane-containing solid colloids.

Figure 13:
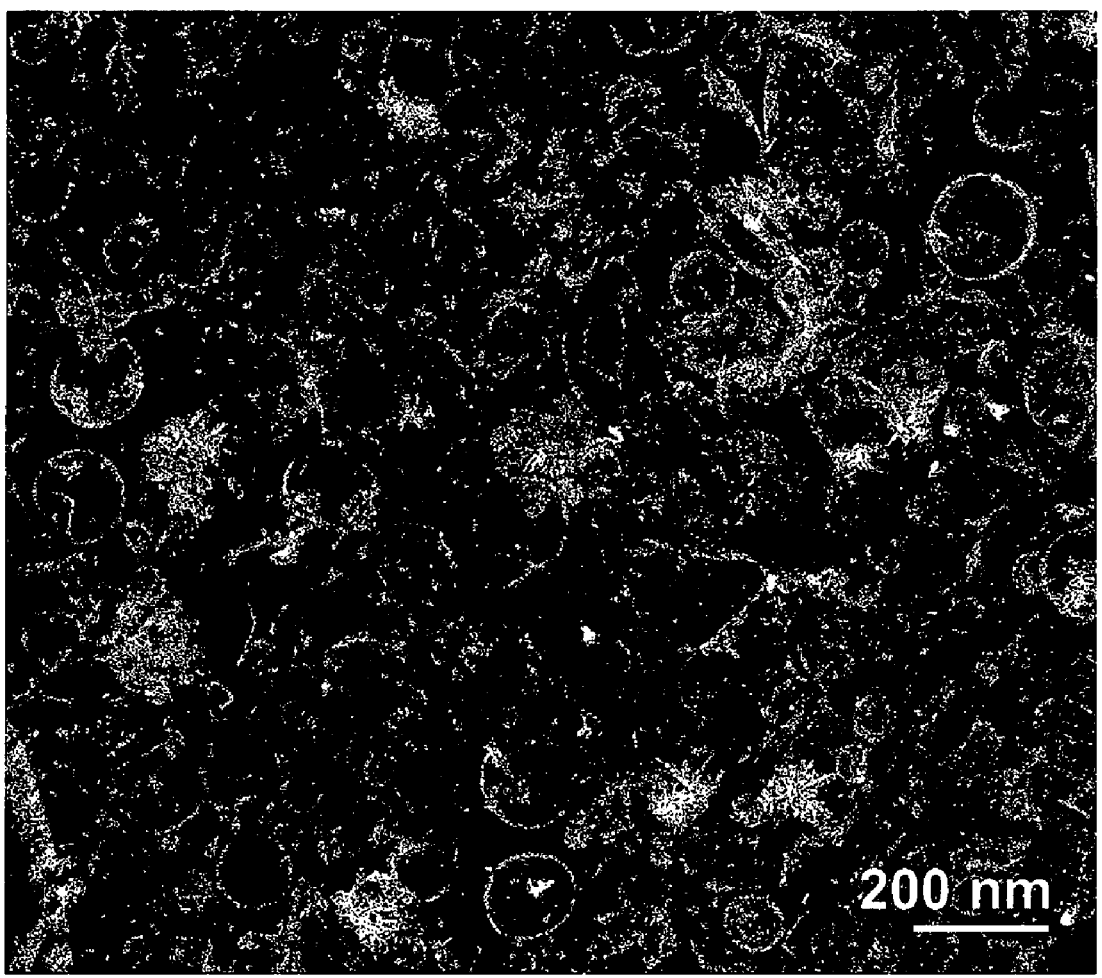
FIG. 13—HAADF image by means of STEM showing silicon-containing nanoparticles according to certain embodiments of the invention having diameters of between 50-200 nm.

Example 12—Scanning Transmission Electron Micrographs (STEM) and Elemental Analysis by Means of Energy-Dispersive X-Ray Spectroscopy of Silicon-Containing Nanoparticles Synthesized in Aqueous Medium FIG. 13 shows an HAADF image by means of STEM showing silicon-containing colloids with diameters of between 50-200 nm. The nature of these colloids according to certain embodiments of the invention is characterized in that they, as shown in FIG. 13, preferably have a spherical geometry, are hollow and have a shell which preferably has a thickness of between 3-10 nm. This colloid architecture according to certain embodiments of the invention is made possible by the method according to certain embodiments of the invention using trisilane precursor ($Si_3H_8$) and deionized water ($H_2O$) as solvent and a special selection of duty cycle (60-70%), amplitude (190-220 μm) trisilane concentration (5-15 vol. %) and temperature (5-10° C.). The term "duty cycle" given in percent is the active period of a sonotrode/ultrasound source of the entire sonication time. Thus, a duty cycle of 60% means that the sonotrode is turned on for 600 milliseconds and turned off for 400 milliseconds. The indication of the amplitude means the sonotrode amplitude, i.e., the maximum spatial back and forth movement of the sonotrode tip.

Figure 14:
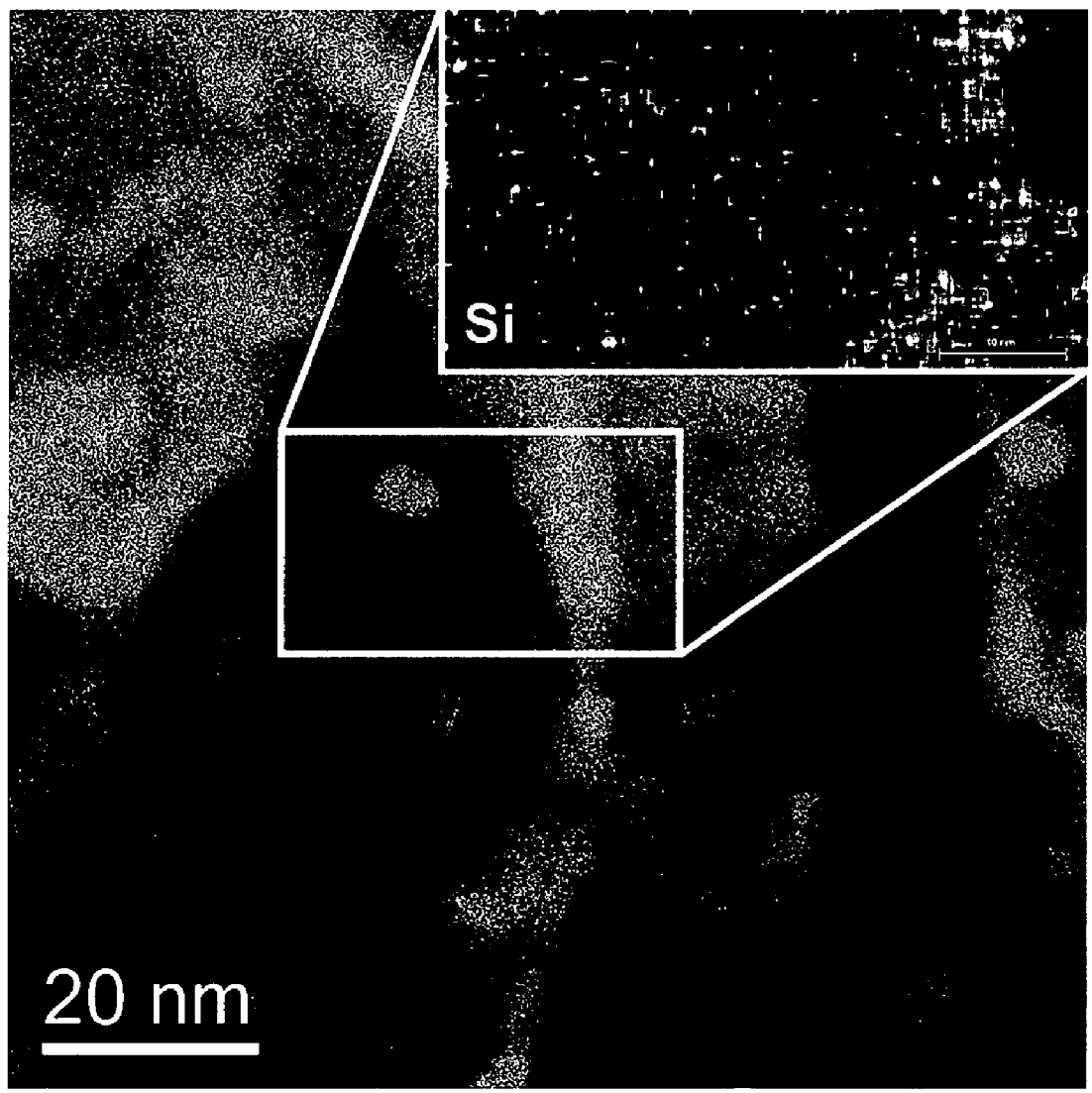
FIG. 14—HAADF image showing the area of the shell of a nanoparticle according to certain embodiments of the invention and in the inset on the upper right-hand side the associated space-resolved element-specific distribution of silicon (Si) by means of energy-dispersive X-ray spectroscopy.

FIG. 14 shows an HAADF image of the area of the shell of a colloid according to certain embodiments of the invention and in the inset on the upper right-hand side the associated space-resolved element-specific distribution by means of energy-dispersive X-ray spectroscopy (=EDX) of silicon (Si). Elemental analysis shows the silicon-containing composition of the colloids.

Figure 15:
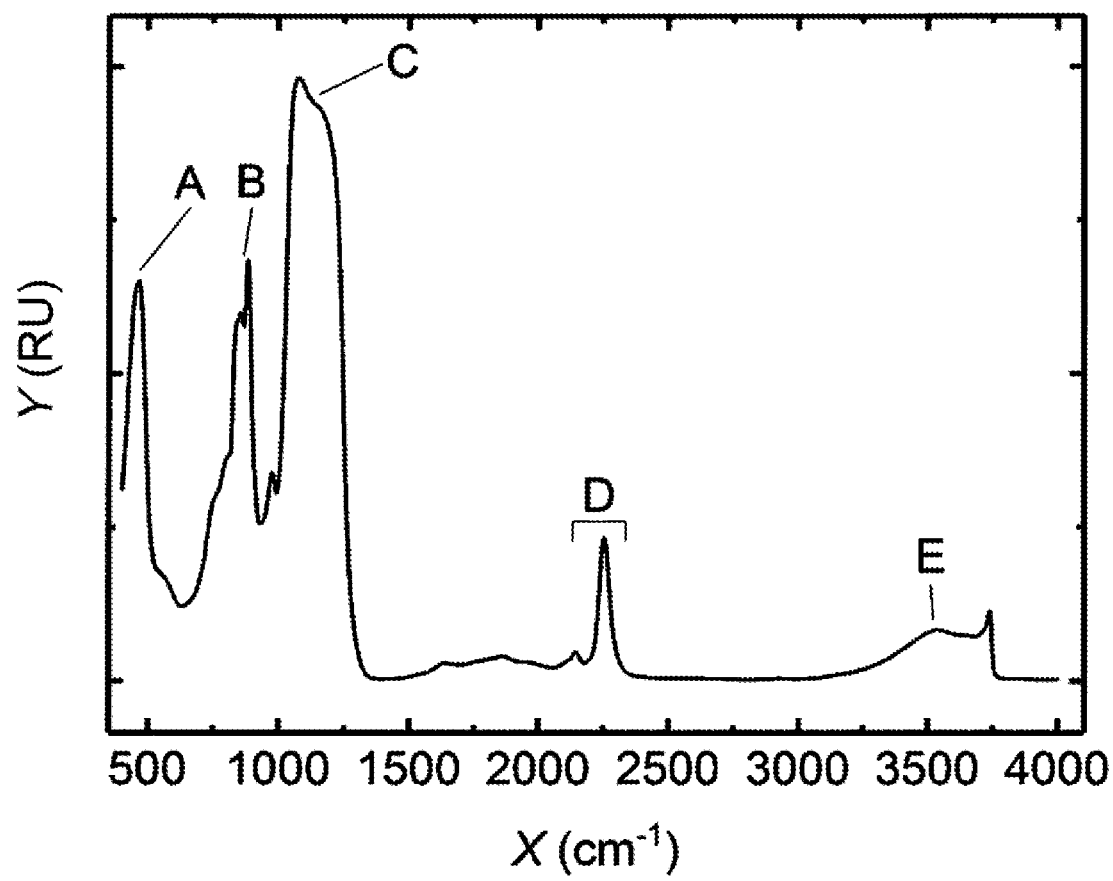
FIG. 15—FTIR spectrum of silane-containing composite colloids produced from trisilane using deionized water ($H_2O$) as solvent.

Example 13—Fourier-Transformed Infrared Spectrum (FTIR) of Hydrogenated Silicon-Containing Composite Colloids According to the Certain Embodiments of Invention Produced by Sonication of an Aqueous Trisilane Solution FIG. 15 shows an FTIR spectrum of silane-containing composite colloids produced from trisilane using deionized water ($H_2O$) as solvent. The composite colloids were taken from a stable dispersion and applied to a silicon wafer, dried and then measured at room temperature. The abscissa indicates the wavenumber in ($cm^{-1}$) and the ordinate Y indicates the signal intensity in relative units (RU). Mode (A) points to the SiO flexural vibration, mode (B) points to the $SiH_x$ flexural vibration, modes (C) point to the Si—O—Si stretch vibration, modes (D) point to $O_ySi$—$H_x$ stretch vibrations and mode (E) point to $H_2O$ stretch vibration. These modes are characteristic of amorphous silane-containing colloids. In particular, based on modes (C) and (D), it can be concluded that these composite colloids are both oxidized (oxygen-containing) and hydrogenated (hydrogen-containing).

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. Hydrogenated amorphous silicon-containing colloids or composite colloids, comprising: a silicon-containing shell surrounding a cavity, wherein:
    the silicon-containing colloids have a spherical geometry,
    the silicon-containing composite colloids have a spherical geometry, a diameter of between 2 nm and 63 nm in scanning electron micrographs, and a diameter of between 50 and 200 nm in scanning transmission electron micrographs,
    the silicon-containing shell has a thickness of between 3 and 10 nm, and
    at least a portion of the amorphous silicon-containing colloids or composite colloids is hydrogenated.

2. A method for producing the hydrogenated amorphous silicon-containing colloids or composite colloids according to claim 1 and for encapsulating substances with said hydrogenated amorphous silicon-containing composite colloids, as well as hydrogenated amorphous silicon-containing composite colloids and substances encapsulated with hydrogenated amorphous silicon-containing composite colloids, the method comprising:
    for producing the composite colloids, subjecting to cavitation by a sonotrode a trisilane cyclooctane solution with an additive, wherein the trisilane concentration is 25 vol. % and the additive concentration is 13 vol. %, sonication by the sonotrode being carried out at a process temperature of 8° C., for a duration of 320 min and at an amplitude of 216 μm, and
    for producing the colloids, subjecting to cavitation by a sonotrode a trisilane precursor ($Si_3H_8$) in water as solvent, wherein the sonotrode has a duty cycle of 60-70%, and an amplitude of between 190-220 μm, and wherein a trisilane concentration of between 5 and 15 vol. %, at a process temperature of between 5-10° C., is used.

3. The method according to claim 2, wherein substances which are solid, liquid or gaseous are used as the additive.

4. The method according to claim 2, wherein the additive or substance is selected from the group consisting of nanoparticles, molecules, pentynes, lithium-containing compounds, dopants, boranes, white phosphorus and general compounds.

5. The method according to claim 2, wherein at least one substance is encapsulated or coated with a silicon-containing layer or embedded in a silicon-containing layer as a result of the method.

6. The method according to claim 5, wherein after coating, the method further comprises sintering, crystallizing, or both sintering and crystallizing in an atmosphere that contains hydrogen, is low-pressure, or both contains hydrogen and is low pressure.

7. The method according to claim 2, wherein UV irradiation, microwave irradiation, active cooling, or any combination thereof is used during production.

8. An energy-storing component, wherein an anode material comprises the hydrogenated amorphous silicon-containing composite colloid according to claim 1.

9. A therapeutic, a medicament carrier, a fluorescent marker, a magnetic resonance imaging marker, a contrast agent and/or a hyperthermia therapeutic, comprising the hydrogenated amorphous silicon-containing composite colloid according to claim 1.

10. The method according to claim 4, wherein:
    the nanoparticle is selected from the group consisting of Au, c-Si, CdSe, CuO, $Cu_2O$, $Cu_2S$, CuS, Li, LiH, $Fe_3O_4$, $Fe_2O_4$, FeS, $FeS_2$, $FeSi_2$, SnS, ZnS, and ZrS, the molecule is selected from the group consisting of alendronates, cisplatin, doxorubicin, epirubicin, fluorouracil, and idarubicin, the compound of pentynes is 1-pentyne or 2-pentyne, the dopant is selected from the group consisting of boron-containing and phosphorus-containing compounds, the borane is selected from the group consisting of diborane, pentaborane and decaborane, and the general compound is selected from the group consisting of phosphanes and phosphines.

11. The hydrogenated amorphous silicon-containing colloids or composite colloids according to claim 1, wherein the silicon-containing composite colloids have a diameter of between 2 nm and 25 nm in scanning electron micrographs.

12. The hydrogenated amorphous silicon-containing colloids or composite colloids according to claim 1, wherein the silicon-containing composite colloids have a diameter of between 2 nm and 7 nm in scanning electron micrographs.

13. The hydrogenated amorphous silicon-containing colloids or composite colloids according to claim 1, wherein at least a portion of an inner surface or an outer surface of the silicon-containing shell is terminated with a hydrogen-containing group.

14. The hydrogenated amorphous silicon-containing colloids or composite colloids according to claim 13, wherein the hydrogen-containing group is selected from the group consisting of —SiH, —SiH$_2$, —SiH$_3$, and any combination thereof.

15. The hydrogenated amorphous silicon-containing colloids or composite colloids according to claim 5, wherein the hydrogenated amorphous silicon-containing colloids or composite colloids encapsulate or are coated by at least one substance.

16. The hydrogenated amorphous silicon-containing colloids or composite colloids according to claim 15, where the at least one substance is a nanoparticle selected from the group consisting of Au, c-Si, CdSe, CuO, Cu$_2$O, Cu$_2$S, CuS, Li, LiH, Fe$_3$O$_4$, Fe$_2$O$_4$, FeS, FeS$_2$, FeSi$_2$, SnS, ZnS, and ZrS.

17. The hydrogenated amorphous silicon-containing colloids or composite colloids according to claim 14, where the at least one substance is a molecule selected from the group consisting of alendronates, cisplatin, doxorubicin, epirubicin, fluorouracil, idarubicin, and any combination thereof.

18. The hydrogenated amorphous silicon-containing colloids or composite colloids according to claim 14, where the at least one substance is 1-pentyne, 2-pentyne, or a combination thereof.

19. The hydrogenated amorphous silicon-containing colloids or composite colloids according to claim 14, where the at least one substance is a borane selected from the group consisting of diborane, pentaborane, decaborane, and any combination thereof.

20. The hydrogenated amorphous silicon-containing colloids or composite colloids according to claim 14, where the at least one substance is a general compound selected from the group consisting of phosphanes, phosphines, and a combination thereof.

* * * * *